(12) United States Patent
Niva et al.

(10) Patent No.: US 7,752,011 B2
(45) Date of Patent: Jul. 6, 2010

(54) PORTABLE APPARATUS FOR DETERMINING A USER'S PHYSIOLOGICAL DATA WITH FILTERED SPEED DATA

(75) Inventors: Arto Niva, Jääli (FI); Jukka Jaatinen, Kempele (FI)

(73) Assignee: Polar Electro Oy, Kempele (FI)

( * ) Notice: Subject to any disclaimer, the term of this patent is extended or adjusted under 35 U.S.C. 154(b) by 347 days.

(21) Appl. No.: 11/777,016

(22) Filed: Jul. 12, 2007

(65) Prior Publication Data
US 2009/0018773 A1    Jan. 15, 2009

(51) Int. Cl.
*G06F 15/00* (2006.01)
*G01C 21/00* (2006.01)

(52) U.S. Cl. ................................ 702/160; 701/213

(58) Field of Classification Search ................ 702/160, 702/142, 182; 340/670; 701/213, 300
See application file for complete search history.

(56) References Cited

U.S. PATENT DOCUMENTS 4,625,732 A    12/1986  Kasa et al.
4,625,733 A    12/1986  Saynajakangas
6,013,007 A *   1/2000  Root et al. ................... 482/8
7,050,907 B1    5/2006  Janky et al.
7,561,200 B2 *  7/2009  Garvey et al. .......... 348/333.01

FOREIGN PATENT DOCUMENTS

| EP | 1066793 A2 | 1/2001 |
| WO | WO 01/42809 A2 | 6/2001 |
| WO | WO 2005/045462 A1 | 5/2005 |

* cited by examiner

*Primary Examiner*—Bryan Bui
(74) *Attorney, Agent, or Firm*—Hoffmann & Baron, LLP

(57) ABSTRACT

A portable apparatus including a first interface configured to input speed data of a user or location data of the user from a positioning unit utilizing external reference points is disclosed. The portable apparatus also includes a second interface configured to input motion data of a user from a self-contained activity determining unit. Furthermore, the portable apparatus includes a processing unit configured to constitute, if the first interface only inputs the location data, speed data from the location data, select filtering characteristics based on the motion data, filter the speed data with the selected filtering characteristics, and determine physiological data of the user with the filtered speed data.

22 Claims, 3 Drawing Sheets

PORTABLE APPARATUS FOR DETERMINING A USER'S PHYSIOLOGICAL DATA WITH FILTERED SPEED DATA

BACKGROUND

1. Field

The invention relates to a portable apparatus comprising an interface configured to input speed data of a user or location data of the user from a positioning unit utilizing external reference points.

2. Description of the Related Art

The positioning unit, such as a GPS (Global Positioning System) receiver, utilizing external reference points is not always able to determine the speed of the user with sufficient reliability, especially if the user is walking or running. This is due to the positioning method itself, wherein the integrated circuits, antennas, power and sampling rate of the positioning unit affect the accuracy. Additionally, external factors, such as reflections, blind spots and weather conditions may affect the quality of the positioning signal received by the positioning unit, and hence the quality of the speed data or the location data.

SUMMARY

The present invention is directed to a portable apparatus, which includes a first interface, a second interface and a processing unit. The first interface is configured to input speed data of a user or location data of the user from a positioning unit utilizing external reference points. The second interface is configured to input motion data of a user from a self-contained activity determining unit. The processing unit is configured to constitute, if the first interface only inputs the location data, speed data from the location data, select filtering characteristics based on the motion data, filter the speed data with the selected filtering characteristics, and determine physiological data of the user with the filtered speed data.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one" or "some" embodiment(s) in several locations, this does not necessarily mean that each such reference is to the same embodiment(s), or that the feature only applies to a single embodiment. Single features of different embodiments may also be combined to provide other embodiments.

Figure 1:
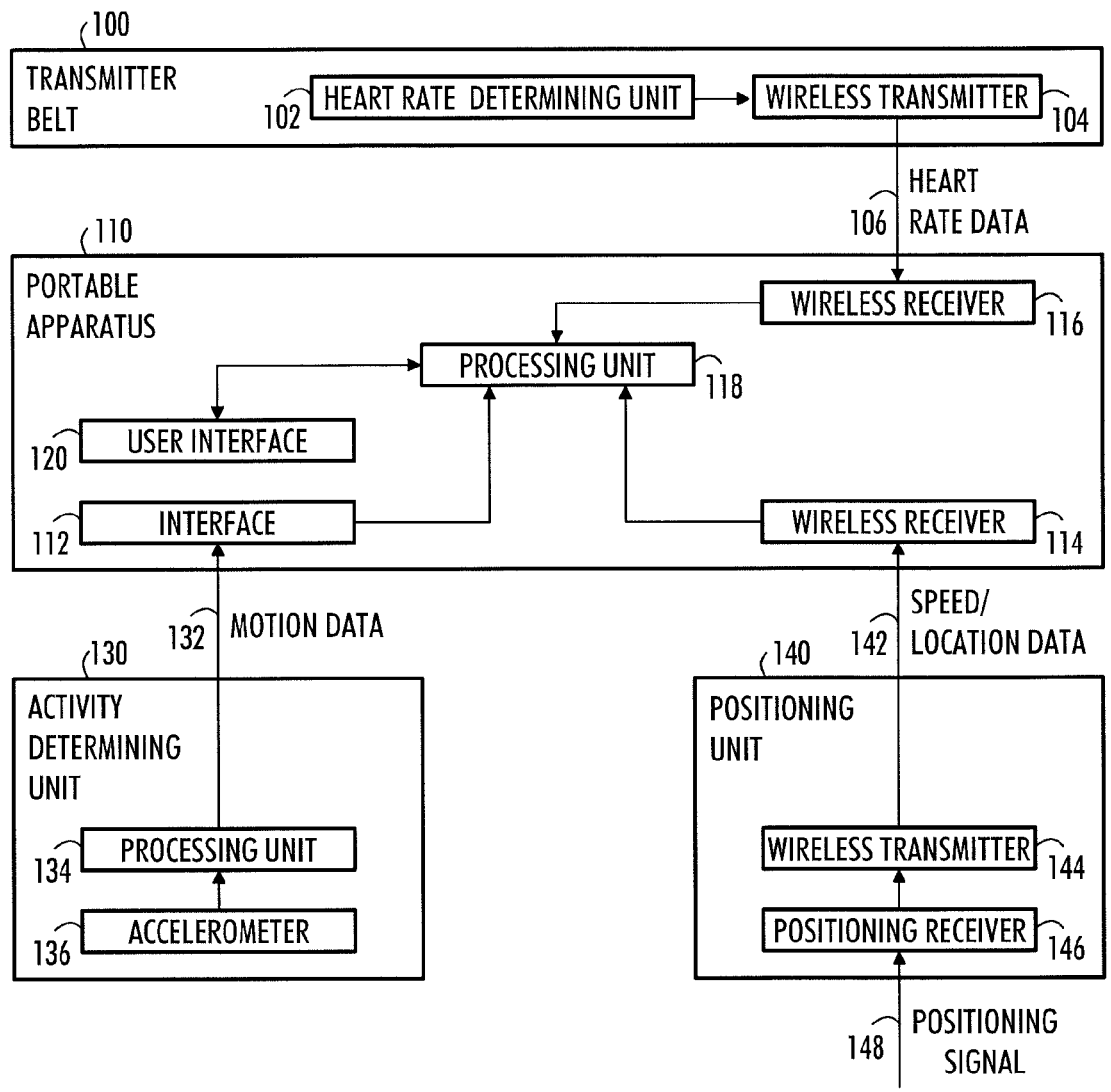
FIG. 1 illustrates embodiments of a portable apparatus.

FIG. 1 illustrates a portable apparatus 110, a self-contained activity determining unit 130, a positioning unit 140, and a transmitter belt 100. FIG. 1 is a simplified block diagram only showing some elements and functional entities, all being logical units whose implementation may differ from what is shown. The connections shown in FIG. 1 are logical connections, the actual physical connections may be different. It is apparent to a person skilled in the art that the described equipment also comprise other functions and structures. It should be appreciated that the functions, structures, elements and the protocols used for communication are irrelevant to the actual invention. Therefore, they do not need to be discussed in more detail here. The specifications of portable apparatuses develop rapidly. Such a development may require extra changes to an embodiment. Therefore, all words and expressions should be interpreted broadly and they are intended to illustrate, not to restrict, the embodiment.

The portable apparatus 110 comprises a first interface 114 configured to input speed data 142 of a user or location data 142 of the user from the positioning unit 140 utilizing external reference points. As illustrated in FIG. 1, the first interface 114 may be a wireless receiver 114 receiving the speed/location data 142.

The positioning unit 140 comprises the actual positioning receiver 146, and possibly also a wireless transmitter 144 capable of transmitting the speed/location data to the portable apparatus 110. The positioning receiver 146 may be a receiver of a global navigation satellite system. Such a system may be the Global Positioning System (GPS), the Global Navigation Satellite System (GLONASS), the Galileo Positioning System (Galileo), the Beidou Navigation System, or the Indian Regional Navigational Satellite System (IRNSS), for example. The positioning receiver 146 determines its location (longitude, latitude, and altitude) using time signals 148 transmitted along a line of sight by radio from satellites orbiting the earth. Besides global navigation satellites, the positioning receiver 146 may also determine its location utilizing other known positioning techniques. It is well known that by receiving radio signals from several different base stations, the mobile phone may determine its location.

The portable apparatus 110 also comprises a second interface 112 configured to input motion data 132 of the user from the self-contained activity determining unit 130. If the portable apparatus 110 and the activity determining unit 130 are separate devices, the second interface 112 may be implemented in the similar fashion as the first interface 114, i.e. the portable apparatus 110 may comprise a wireless receiver (not illustrated in FIG. 1) and the activity determining unit 130 may comprise a wireless transmitter (not illustrated in FIG. 1). If the portable apparatus 110 and the activity determining unit 130 are in the same housing, the second interface 112 may be implemented with suitable interface technologies, such as a message interface, a method interface, a sub-routine call interface, a block interface, or any means enabling communication between functional sub-units. This applies to the first interface 114 as well if the positioning unit 140 is within the same housing as the portable apparatus 110.

If the first interface 114 and/or the second interface 112 utilizes wireless transmission, any suitable standard/non-standard wireless communication technique may be used. Such techniques include Bluetooth® radio transmission or proprietary radio transmission. The proprietary radio transmission may operate in 2.4 GHz or 5 kHz frequency, for example.

As illustrated in FIG. 1, the self-contained activity determining unit 130 may be implemented so that at least one accelerometer 136 feeds raw acceleration data to its own processing unit 134 capable of determining speed and/or distance data from the raw acceleration data and feed the speed and/or distance data as motion data 132 to the portable apparatus 110. Alternatively, the accelerometer 136 may feed the raw acceleration data as motion data 132 to the portable apparatus 110, and a processing unit 118 of the portable apparatus 110 processes the raw acceleration data as needed.

The accelerometer 136 measures its own motion, acceleration, i.e. the rate of change of velocity, and converts the acceleration into an electric signal. Acceleration can be expressed by the unit of measurement g. One g is the acceleration caused to an object by the earth's gravity. Accelerations between −2 to +2 g can usually be measured from human movement. Due to its implementation, the accelerometer 136 may belong to microelectromechanical systems (MEMS).

Various techniques may be used for measuring acceleration. Piezo-resistor technology employs material whose resistance changes as it compresses. The acceleration of mass produces a force in a piezo resistor. If constant current is supplied through the piezo resistor, its voltage changes according to the compression caused by acceleration. In piezo-electric technology, a piezo-electric sensor generates charging when the sensor is accelerated. In silicon bridge technology, a silicon chip is etched so that a silicon mass remains on it at the end of a silicon beam. When acceleration is directed to the silicon chip, the silicon mass focuses a force on the silicon beam, thus changing the resistance of the silicon beam. Micro-machined silicon technology is based on the use of a differential capacitor. Voice coil technology is based on the same principle as a microphone. Examples of suitable movement sensors are: Analog Devices ADXL105, Pewatron HW or VTI Technologies SCA series. The implementation of the accelerometer 136 may also be based on other appropriate techniques, for example on a gyroscope integrated into a silicon chip or on a micro vibration switch incorporated into a surface mounting component.

It is also to be noted that the accelerometer 136 may measure the acceleration in one, two or three dimensions. Instead of just one accelerometer 136, also two or even three separate accelerometers each measuring a different dimension may be utilized.

Furthermore, the portable apparatus 110 comprises a processing unit 118 configured to constitute, if the first interface 114 only inputs the location data, speed data from the location data. In an embodiment the so processing unit 118 is configured to constitute the speed data from the location data by determining the traveled distance of the user from the location data and dividing the traveled distance by time used for traveling the traveled distance.

The processing unit 110 is also configured to select filtering characteristics based on the motion data 132, filter the speed data with the selected filtering characteristics, and determine physiological data of the user with the filtered speed data. The filtering characteristics are selected so that the speed data is more accurate as regards to its use in determining the physiological data of the user. The physiological data of the user may be a quantity describing performance of the user, for example. The filtered speed data may also be used for determining other physiological data of the user, such as a Running Index (used in devices developed by Polar Electro). Running Index offers an easy way of monitoring performance changes. Performance (how fast/easily you run at a given pace) is directly influenced by aerobic fitness ($VO_{2max}$) and exercise economy (how efficient your body is at running), and Running Index is a measurement of this influence.

In an embodiment, the processing unit 118 is configured to select, if the level of the motion data 132 is below a predetermined lower threshold, such filtering characteristics that the speed data is set to zero.

In another embodiment, the processing unit 118 is configured to select, if the level of the motion data 132 is above a predetermined lower threshold but below a predetermined upper threshold, such filtering characteristics that the fluctuation in the speed data is reduced. This is usable while the user is walking.

In a further embodiment, the processing unit 118 is configured to select, if the level of the motion data 132 is above a predetermined upper threshold, such filtering characteristics that the fluctuation in the speed data is reduced less than in the case where the level of the motion data is above a predetermined lower threshold but below the predetermined upper threshold. This is usable while the user is walking fast or running.

In effect, the portable apparatus utilizes the motion data 132 for calibrating the speed data. The faster the user is moving, the less calibrating is needed as the error in the speed data is inversely proportional to the speed. If the user moves fast, the speed data becomes more reliable.

There may also be defined a user-specific dependency between the speed data and the motion data, i.e. if the speed data is unavailable or unreliable, the speed may be estimated based on the motion data. There may be stored a general dependency in the portable apparatus 110 as a starting point, but the teaching of the portable apparatus 110 with the activity determining unit 130 improves the accuracy considerably.

The processing unit 118 may be deemed as a miniature electronic digital computer, which may comprise a working memory (RAM), a central processing unit (CPU), and a system clock. The CPU may comprise a set of registers, an arithmetic logic unit, and a control unit. The control unit is controlled by a sequence of program instructions transferred to the CPU from the RAM. The control unit may contain a number of microinstructions for basic operations. The implementation of microinstructions may vary, depending on the CPU design. The program instructions may be coded by a programming language, which may be a high-level programming language, such as C, Java, etc., or a low-level programming language, such as a machine language, or an assembler. The electronic digital computer may also have an operating system, which may provide system services to a computer program written with the program instructions.

Some part of the functionality of the processing unit 118 may be implemented as a computer program embodied on a distribution medium, comprising program instructions which, when loaded into the processing unit 118, constitute the aforementioned functionality. The computer program may be in source code form, object code form, or in some intermediate form, and it may be stored in some sort of carrier, which may be any entity or device capable of carrying the program. Such carriers include a record medium, computer memory, read-only memory, electrical carrier signal, telecommunications signal, and software distribution package, for example.

The processing unit 118 may be implemented as a processor with software, but various hardware implementations are also feasible, such as a circuit consisting of logic components or one or more application-specific integrated circuits ASIC. The processor may be, for example, an 8-bit microprocessor, type S1C8F manufactured by Seiko-Epson®. If necessary, there may be more than one processor. A hybrid of these different implementations is also feasible. When designing the implementation, a person skilled in the art will consider the requirements set for the size and power consumption of the apparatus 110, necessary processing capacity, production costs, and production volumes, for example.

The portable apparatus 110 may be a wrist-worn apparatus, or a subscriber terminal of a radio system such as a mobile phone, for example. The portable apparatus 110 may also be a sports watch for use as an instrument in sports, or a so-called pedometer. In the wrist-worn apparatus 110, the electronics components shown in FIG. 1 are protected by a housing (which is usually waterproof). In addition, the wrist-worn apparatus 110 comprises a wristband for attaching the device to the wrist.

Depending on the design and features of the portable apparatus 110, the integration of the portable apparatus 110, activity determining unit 130 and the positioning unit 140 may vary.

The activity determining unit 130 may be integrated into the portable apparatus 110. Hence, the accelerometer 134 may be, during use, in the wrist of the user, in the hand of the user, attached to a string and hanging from the user, or in the pocket of the user, for example.

The activity determining unit 130 may also be separated from the portable apparatus 110. European patent application 1 066 793 describes the use of at least a pair of accelerometers, which may be mounted on an athletic shoe, for example. Thus, the activity determining unit 130 may be a foot-worn device. The difference in the placing of the accelerometer 136 may need to be considered in applying the motion data 132 in the right way. A foot-worn accelerometer 136 may produce kinematic results for a stride, i.e. acceleration in a selected direction, velocity in a selected direction or distance in a selected direction. Hand/torso motion data, in the form of signal frequency, signal power or some other parameter derived from the signal, may be obtained from a hand/torso-worn accelerometer 136.

The positioning unit 140 may also be integrated into the housing of the portable apparatus 110. If the positioning receiver 146 utilizes signals from a cellular radio network as positioning signals 148 and the portable apparatus is a mobile phone, such a combination may be optimal.

However, the positioning unit 140 may also be separated from the portable apparatus 110. The positioning unit 140 may be placed on the upper arm of the user in order to improve the reception of the positioning signals 148 from the satellites, for example.

The portable apparatus 110 may comprise a user interface 120. The user interface 120 typically comprises a display, means for producing sound, and a keyboard. The display may be a liquid crystal display, for example, but it may also be implemented by any appropriate prior art technique. The means for producing sound may be a loudspeaker or a simpler means for producing beeps or other sound signals. The keyboard may comprise a complete qwerty keyboard, a mere numeric keypad or only a few push buttons and/or rotary buttons. In addition, the user interface 120 may comprise other prior art user interface elements, for example various means for focusing a cursor (mouse track ball, various arrow keys, etc.) or elements enabling audio control. The physiological data of the user may be shown on the user interface 120, on the display for example.

The portable apparatus 110 may also be capable of communicating with a transmitter belt 100. The transmitter belt 100 is worn around the chest of the user and it comprises a heart rate determining unit 102 which measures the user's heart rate, and a wireless transmitter 104 configured to transmit heart rate data 106 to a wireless receiver 116 of the portable apparatus 110. The portable apparatus 110 may thus be a heart rate monitor for measuring the users heart rate, and possibly other parameters that can be measured non-invasively (such as blood pressure). In U.S. Pat. No. 4,625,733, which is incorporated herein by reference, Säynäjäkangas describes a wireless and continuous heart rate monitoring concept where a transmitter to be attached to the user's chest measures the user's ECG-accurate (electrocardiograms heart rate and transmits the heart rate information telemetrically to the heart rate receiver attached to the user's wrist using magnetic coils in the transmission. The heart rate monitor can also be implemented so that, instead of the solution consisting of a transmitter/receiver, the heart rate is measured directly from the wrist based on the pressure, for example. Other prior art methods for measuring the heart rate may also be employed, provided that they are suitable for use in a portable personal data processing device.

Polar Electro® (www.polarusa.com) designs and manufactures heart rate monitors and their accessories. At the writing of this patent application, the portable apparatus 110 may be implemented based on the Polar RS800sd Running Computer, the activity determining unit 130 may be implemented based on the foot-worn Polar s3 stride sensor W.I.N.D., and the transmitter belt 100 may be implemented based on the Polar WearLink 31 coded transmitter, for example. The foot-worn activity determining unit 130 may also be called a footpod. Naturally, also an accelerometer 136 placed in the housing of the heart rate monitor may be used to implement the activity determining unit 130. At the writing of this patent application, Polar Electro does not have a product in its line that could be used as the positioning unit 140, but a normal Bluetooth enabled GPS receiver may be used, a GlobalSat SiRF III GPS receiver, for example. Naturally, as the products evolve, also the feasible platforms for the implementation of the embodiments described in this patent application evolve and emerge.

Figure 2:
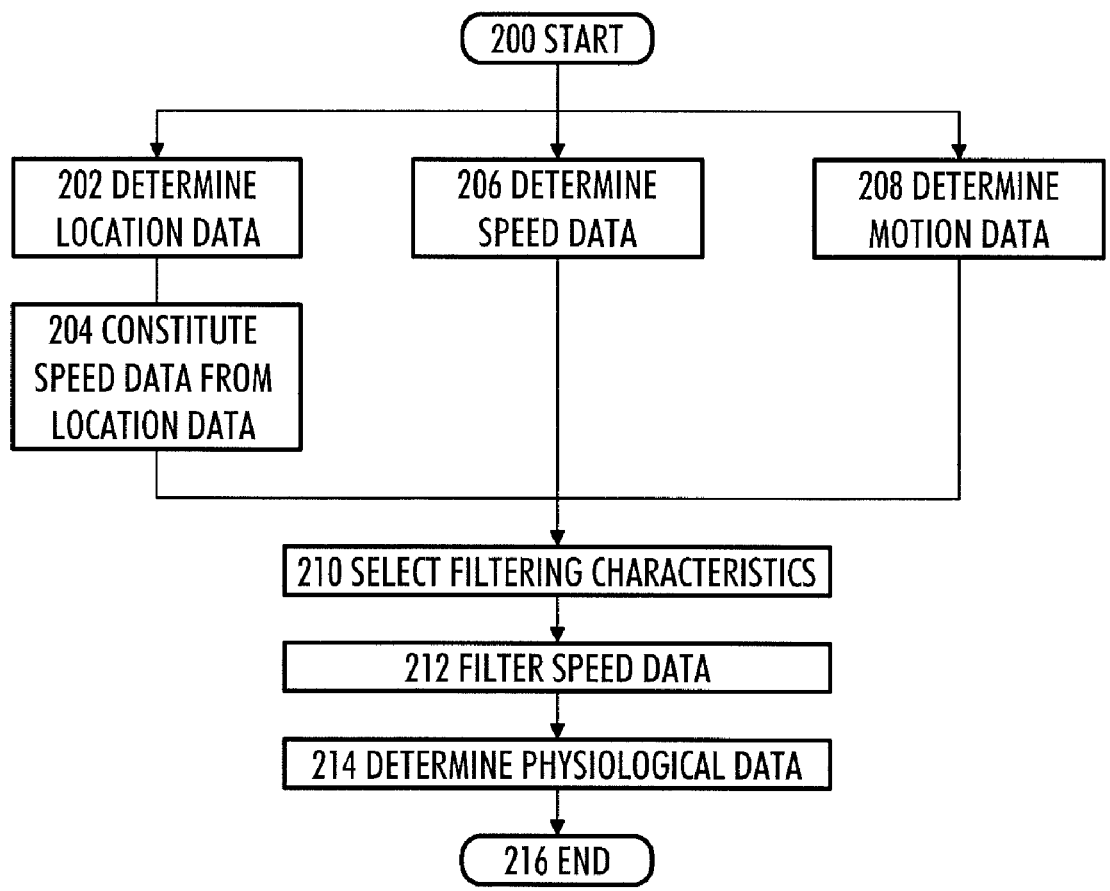
FIGS. 2 and 3 illustrate embodiments of a method.
Figure 3:
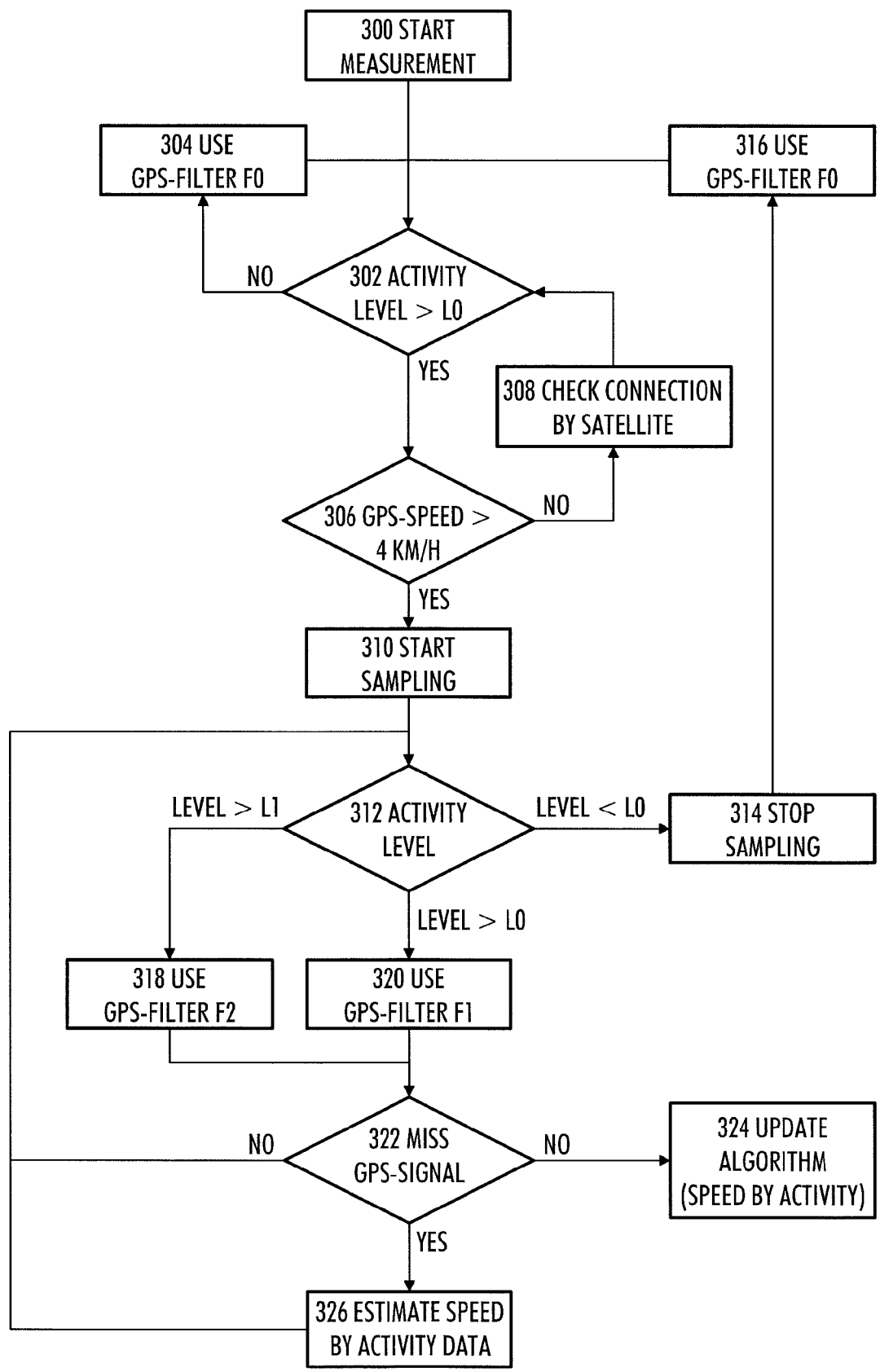

Next, a method will be described with reference to FIGS. 2 and 3. The method may be performed in at least one portable apparatus. The operations described in FIGS. 2 and 3 are in no absolute chronological order, and some of the operations may be performed simultaneously or in an order differing from the given one. Other functions, not described in this application, may also be executed between the operations or within the operations. Some of the operations or part of the operations may also be left out or replaced by a corresponding operation or part of the operation.

The method starts in 200. In 202, location data of the user is determined by a positioning unit utilizing external reference points. In 206, speed data of the user is determined by a positioning unit utilizing external reference points. Operations 202 and 206 may be optional in the sense that only one of them is performed.

If only the location data is determined, speed data is constituted from the location data in 204. In an embodiment, the speed data is constituted from the location data by determining the traveled distance of the user from the location data and dividing the traveled distance by time used for traveling the traveled distance.

Simultaneously, motion data of a user is determined by a self-contained activity determining unit in 208.

In 210, filtering characteristics are selected based on the motion data.

In 212, the speed data is filtered with the selected filtering characteristics.

In 214, physiological data of the user is determined with the filtered speed data. The physiological data of the may comprise a quantity describing performance of the user, for example.

The method ends in 216.

In an embodiment (called a GPS filter F0 in FIG. 3), if the level of the motion data is below a predetermined lower threshold (L0 in FIG. 3), such filtering characteristics are selected that the speed data is set to zero.

In another embodiment (called a GPS filter F1 in FIG. 3), if the level of the motion data is above a predetermined lower threshold but below a predetermined upper threshold (L1 in FIG. 3), such filtering characteristics are selected that the fluctuation in the speed data is reduced.

In a further embodiment (called a GPS filter F2 in FIG. 3), if the level of the motion data is above a predetermined upper threshold, such filtering characteristics are selected that the fluctuation in the speed data is reduced less than in the case where the level of the motion data is above a predetermined lower threshold but below the predetermined upper threshold.

Some further aspects of the method are illustrated in FIG. 3. The measurement starts in 300. In 302 it is checked whether the activity level (based on the motion data) is greater than L0. If it is not, the GPS filter F0 is used in 304, else it is checked whether the GPS speed is higher than 4 km/h in 306. If the GPS speed is not higher than 4 km/h, the connection to the satellite(s) is checked in 308.

If the GPS speed is higher than 4 km/h: sampling is started in 310.

A further check on the activity level is made in 312:
  if the activity level is below L0, the sampling is stopped on 314 and the GPS filter F0 is used in 316;
  if the activity level is above L0 but below L1, the GPS filter L1 is used in 320, and
  if the activity level is above L1, the GPS filter F2 is used in 318.

After 318 and 320, it is checked whether the GPS signal is missed in 322. If the GPS signal is not missed, the algorithm (speed by activity) may be updated in 324, and 312 is thereupon entered again. If the GPS signal is missed, speed is estimated by activity data in 326, and 312 is thereupon entered again.

It will be obvious to a person skilled in the art that, as technology advances, the inventive concept can be implemented in various ways. The invention and its embodiments are not limited to the examples described above but may vary within the scope of the claims.

What is claimed is:

1. A portable apparatus comprising:
  a first interface configured to input speed data of a user or location data of the user from a positioning unit utilizing external reference points;
  a second interface configured to input motion data of the user from a self-contained activity determining unit; and
  a processing unit configured to determine, if the first interface only inputs the location data, speed data from the location data, select filtering characteristics based on the motion data, filter the speed data with the selected filtering characteristics, and determine physiological data of the user using the filtered speed data.

2. The apparatus of claim 1, wherein the processing unit is further configured to select, if a level of the motion data is below a predetermined lower threshold, filtering characteristics such that the speed data is set to zero.

3. The apparatus of claim 1, wherein the processing unit is further configured to select, if a level of the motion data is above a predetermined lower threshold but below a predetermined upper threshold, filtering characteristics such that the fluctuation in the speed data is reduced.

4. The apparatus of claim 1, wherein the processing unit is further configured to select, if a level of the motion data is above a predetermined upper threshold, filtering characteristics such that the fluctuation in the speed data is reduced less than in the case where the level of the motion data is above a predetermined lower threshold but below the predetermined upper threshold.

5. The apparatus of claim 1, wherein the processing unit is further configured to determine the speed data from the location data by determining the traveled distance of the user from the location data and dividing the traveled distance by time used for traveling the traveled distance.

6. The apparatus of claim 1, wherein the physiological data of the user comprises a quantity describing performance of the user.

7. The apparatus of claim 1, wherein the apparatus comprises a wrist-worn apparatus.

8. A method comprising:
  determining speed data of a user or location data of the user by a positioning unit utilizing external reference points;
  determining motion data of the user by a self-contained activity determining unit;
  if only the location data is determined, determining speed data from the location data by a processing unit;
  selecting filtering characteristics based on the motion data by the processing unit;
  filtering the speed data with the selected filtering characteristics by the processing unit; and
  determining physiological data of the user using the filtered speed data by the processing unit.

9. The method of claim 8, further comprising:
  selecting, if the level of the motion data is below a predetermined lower threshold, filtering characteristics such that the speed data is set to zero.

10. The method of claim 8, further comprising:
  selecting, if the level of the motion data is above a predetermined lower threshold but below a predetermined upper threshold, filtering characteristics such that the fluctuation in the speed data is reduced.

11. The method of claim 8, further comprising:
  selecting, if the level of the motion data is above a predetermined upper threshold, filtering characteristics such that the fluctuation in the speed data is reduced less than in the case where the level of the motion data is above a predetermined lower threshold but below the predetermined upper threshold.

12. The method of claim 8, further comprising:
  constituting the speed data from the location data by determining the traveled distance of the user from the location data and dividing the traveled distance by time used for traveling the traveled distance.

13. The method of claim 8, wherein the physiological data of the user comprises a quantity describing performance of the user.

14. The method of claim 8, performed in at least one portable apparatus.

15. A portable apparatus comprising:
  means for inputting speed data of a user or location data of the user;
  means for inputting motion data of the user;
  if only the location data is inputted, means for determining speed data from the location data;
  means for selecting filtering characteristics based on the motion data;
  means for filtering the speed data with the selected filtering characteristics; and
  means for determining physiological data of the user using the filtered speed data.

16. The apparatus of claim 15, further comprising means for selecting, if the level of the motion data is below a predetermined lower threshold, filtering characteristics such that the speed data is set to zero.

17. The apparatus of claim 15, further comprising means for selecting, if the level of the motion data is above a predetermined lower threshold but below a predetermined upper threshold, filtering characteristics such that the fluctuation in the speed data is reduced.

18. The apparatus of claim 15, further comprising means for selecting, if the level of the motion data is above a predetermined upper threshold, filtering characteristics such that the fluctuation in the speed data is reduced less than in the case where the level of the motion data is above a predetermined lower threshold but below the predetermined upper threshold.

19. The apparatus of claim 15, further comprising means for constituting the speed data from the location data by determining the traveled distance of the user from the location data and dividing the traveled distance by time used for traveling the traveled distance.

20. The apparatus of claim 15, wherein the physiological data of the user comprises a quantity describing performance of the user.

21. The apparatus of claim 15, wherein the apparatus comprises a wrist-worn apparatus.

22. A system comprising:
a positioning unit utilizing external reference points;
a self-contained activity determining unit; and
a portable apparatus comprising:
    a first interface configured to input speed data of a user or location data of the user from the positioning unit;
    a second interface configured to input motion data of the user from the self-contained activity determining unit; and
    a processing unit configured to determine, if the first interface only inputs the location data, speed data from the location data, select filtering characteristics based on the motion data, filter the speed data with the selected filtering characteristics, and determine physiological data of the user using the filtered speed data.

* * * * *